United States Patent
Gottlieb et al.

(10) Patent No.: US 9,307,936 B2
(45) Date of Patent: Apr. 12, 2016

(54) POLAR PLOT TO REPRESENT GLUCOSE SENSOR PERFORMANCE

(75) Inventors: Rebecca K. Gottlieb, Culver City, CA (US); Ying Luo, Stevenson Ranch, CA (US); Ning Yang, Northridge, CA (US); James Geoffrey Chase, Christchurch (NZ)

(73) Assignee: Medtronic Minimed, Inc., Northridge, CA (US)

( * ) Notice: Subject to any disclaimer, the term of this patent is extended or adjusted under 35 U.S.C. 154(b) by 911 days.

(21) Appl. No.: 13/467,728

(22) Filed: May 9, 2012

(65) Prior Publication Data

US 2013/0109943 A1   May 2, 2013

Related U.S. Application Data

(60) Provisional application No. 61/551,863, filed on Oct. 26, 2011.

(51) Int. Cl.
   *A61B 5/00* (2006.01)
   *A61B 5/145* (2006.01)
   *A61B 5/1495* (2006.01)
   *A61B 5/1486* (2006.01)

(52) U.S. Cl.
   CPC ........... *A61B 5/14532* (2013.01); *A61B 5/1495* (2013.01); *A61B 5/7239* (2013.01); *A61B 5/7275* (2013.01); *A61B 5/743* (2013.01); *A61B 5/14865* (2013.01); *A61B 5/4839* (2013.01); *A61B 5/6849* (2013.01)

(58) Field of Classification Search
   CPC combination set(s) only.
   See application file for complete search history.

(56) References Cited

U.S. PATENT DOCUMENTS

| | | | |
|---|---|---|---|
| 5,050,107 A * | 9/1991 | Cannon et al. | 358/1.3 |
| 7,833,157 B2 | 11/2010 | Gottlieb et al. | |
| 2007/0066873 A1 * | 3/2007 | Kamath et al. | 600/300 |
| 2008/0161664 A1 | 7/2008 | Mastrototaro et al. | |
| 2008/0208027 A1 * | 8/2008 | Heaton | 600/365 |
| 2010/0162786 A1 | 7/2010 | Keenan et al. | |
| 2010/0168538 A1 | 7/2010 | Keenan et al. | |
| 2011/0313390 A1 | 12/2011 | Roy et al. | |
| 2012/0108933 A1 | 5/2012 | Liang et al. | |

FOREIGN PATENT DOCUMENTS

| | | |
|---|---|---|
| EP | 1933246 | 6/2008 |
| WO | WO2007/102842 | 9/2007 |

OTHER PUBLICATIONS

PCT/US2012/037306/ PCT application as filed on May 10, 2012, 43 pages.
PCT/US2012/037306/ International Search Report and written opinion mailed Aug. 16, 2012, 11 pages.
Critchley, Lester A., A Critical Review of the Ability of Continuous Cardiac Output Monitors to Measure Trends in Cardiac Output, Department of Anaesthesia & Intensive Care, www.anesthesia-analgesia.org, vol. 111, No. 5, pp. 1180-1192, Nov. 2010.
Van Den Berghe, "Intensive Insulin Therapy in Critically Ill Patients", Article, The New England Journal of Medicine, Nov. 8, 2001, pp. 1359-1367, vol. 345, No. 19.
Savitzky, "Smoothing and Differentiation of Data by Simplified Least Squares Procedures", Analytical Chemistry, Jul. 8, 1964, pp. 1627-1639, vol. 36, No. 8.
Jauberteau, "Numerical Differentiation with Noisy Signal",: Applied Mathematics and Computation Journal, 2009, pp. 2283-2297, vol. 215.

* cited by examiner

*Primary Examiner* — Michael Kahelin
*Assistant Examiner* — Mitchell E Alter
(74) *Attorney, Agent, or Firm* — Berkeley Law & Technology Group, LLP (57) ABSTRACT

Disclosed are methods, apparatuses, etc. for providing a visual expression of the performance of one or more blood glucose sensors. In one particular example, a relative comparison of a rate of change sensor blood glucose and a rate of change in reference blood glucose may be expressed in a polar plot or graph. The polar plot or graph may then be generated onto a visual medium.

18 Claims, 11 Drawing Sheets

POLAR PLOT TO REPRESENT GLUCOSE SENSOR PERFORMANCE

This application claims the benefit of priority to U.S. Provisional Patent Appl. No. 61/551,863 titled "A New Continuous Glucose Monitoring Trend Metric—the CGM Trend Compass," filed on Oct. 26, 2011, assigned to the assignee of claimed subject matter, and incorporated herein by reference in its entirety.

BACKGROUND

1. Field

Subject matter disclosed herein relates to techniques to evaluate blood glucose sensors.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, which is a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

To determine an appropriate therapy for treating a patient's diabetic conditions, a blood glucose concentration is typically measured using one or more techniques such as, for example, metered blood glucose sample measurements (e.g. using finger sticks) or continuous glucose monitoring from processing signals generated by a blood glucose sensor inserted into subcutaneous tissue. Today, there are few effective techniques for evaluating the performance of blood glucose sensors used in a single patient or multiple patients under different glycemic conditions.

SUMMARY

Briefly, example embodiments may relate to methods, systems, apparatuses, and/or articles, etc. for a method comprising: computing a first rate of change in blood glucose concentration as observed from blood glucose reference samples obtained from a body; computing a second rate of change in said blood glucose concentration as observed at a blood glucose sensor; expressing a relative comparison of said first rate of change and said second rate of change as an angle in a polar plot; and generating signals to present said polar plot in a visual medium. In another embodiment, a radius of values plotted in said polar plot are based, at least in part, on blood glucose measurements obtained from said blood glucose reference samples. The radius may be proportional to a magnitude of said blood glucose concentration as measured from said blood glucose measurements. In another embodiment, an alert region may be defined on the polar plot comprising a hypoglycemic region within a threshold radius, and an angular section may be defined, at least in part, by a positive rate of change in blood glucose according to the computed second rate of change and a negative rate of change according to the second rate of change. In another embodiment, the angle may be computed based, at least in part, as the arctangent of a ratio of the second computed rate of change to the first computed rate of change.

In another embodiment, the visual medium comprises a printed document. In an alternative embodiment, the visual medium comprises an image presented on a computer display.

In another embodiment, computing the second rate of change further comprises: obtaining a first blood glucose reference sample measurement value at a beginning of a period; obtaining a second blood glucose reference sample measurement value at an end of the period; and dividing a difference between the first and second blood glucose reference sample measurement values by the period. In yet another embodiment, the second blood glucose reference sample measurement value may be expressed as a radius in the polar plot. In a particular implementation, a length of said radius may be determined as an increasing function of the second blood glucose reference sample measurement value.

In another embodiment, a computing platform comprises: one or more processors to: compute a first rate of change in blood glucose concentration as observed from blood glucose reference samples obtained from a body; compute a second rate of change in said blood glucose concentration as observed at a blood glucose sensor; express a relative comparison of the first rate of change and the second rate of change as an angle in a polar plot; and generate signals to present said polar plot in a visual medium. In a particular implementation, the computing platform may further comprise a display device to present an image of the polar plot responsive to the generated signals. In another implementation, the computing platform further comprises a storage medium to store a digital image of the polar plot in a compressed format. In another embodiment, the signals comprise commands to a printer for printing the polar plot onto a printed document. In another implementation, the computing platform further comprises a communication device and the one or more processors are further to initiate transmission of the generated signals to a communication network.

In another embodiment, an article comprises: a non-transitory storage medium comprising machine-readable instructions stored thereon which are executable by a special purpose computing apparatus to: compute a first rate of change in blood glucose concentration as observed from blood glucose reference samples obtained from a body; compute a second rate of change in said blood glucose concentration as observed at a blood glucose sensor; express a relative comparison of the first rate of change and the second rate of change as an angle in a polar plot; and generate signals to present the polar plot in a visual medium. In another implementation, the instructions are further executable by said special purpose computing apparatus to compress a digital image of said polar plot in a format for storage in a non-transitory storage medium or for transmission in a communication network. In another implementation, the instructions are further executable by the special purpose computing apparatus to compute the second rate of change by: obtaining a first blood glucose reference sample measurement value at a beginning of a period; obtaining a second blood glucose reference sample measurement value at an end of the period; and dividing a difference between the first and second blood glucose reference sample measurement values by the period. In another implementation, the second blood glucose reference sample measurement value is expressed as a radius in said polar plot. In another implementation, the generated signals comprise signals for presenting an image of the polar plot on a display.

In another embodiment, an apparatus comprises: means for computing a first rate of change in blood glucose concentration as observed from blood glucose reference samples obtained from a body; means for computing a second rate of change in said blood glucose concentration as observed at a blood glucose sensor; means for expressing a relative comparison of said first rate of change and said second rate of change as an angle in a polar plot; and means for generating signals to present said polar plot in a visual medium.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device and/or processor may be adapted to perform at least a portion of described method(s) according to one or more particular implementations based upon the one or more signals generated by the sensor.

BRIEF DESCRIPTION OF THE FIGURES

Non-limiting and non-exhaustive features are described with reference to the following figures, wherein like reference numerals refer to like and/or analogous parts throughout the various figures.

DETAILED DESCRIPTION

The emergence of increasingly accurate and reliable blood glucose sensors for use in continuous blood glucose monitoring of diabetic patients has allowed for increasing reliance on continuous blood glucose monitoring for closed-loop insulin therapy. Increasing accuracy and reliability of blood glucose sensors have also allowed for less frequent blood glucose reference samples for use in calibration of blood glucose sensors for continuous blood glucose monitoring.

A closed-loop or semi closed loop insulin delivery system may employ a blood glucose sensor which is subcutaneously inserted into a patient for continuous blood glucose monitoring and a pump that is controlled to deliver insulin to the patient so as to maintain the patient's blood glucose level within a target range. For example, a controller may process sensor glucose measurements to compute command signals for controlling an insulin infusion pump. In addition to using instantaneous observations of blood glucose levels, a controller may also evaluate how a patient's blood glucose level may be trending (e.g., rising or falling). As such, in computing commands for an insulin infusion pump for maintaining a patient's blood glucose concentration within a target range, a controller may also evaluate a rate of change in observed blood glucose. For example, a controller may employ a proportional-integral-derivative (PID) control algorithm in conjunction with controlling a patient's blood glucose level within a particular range as described in U.S. patent application Ser. No. 12/820,944, filed on Jun. 22, 2010, and assigned to the assignee of claimed subject matter.

As discussed above, there are few effective techniques for evaluating the performance of blood glucose sensors used in a single patient or multiple patients under different conditions. In particular, there are few effective techniques that provide a visual snapshot of the health or performance of a blood glucose sensor in providing an accurate and reliable observation of a rate of change in a patient's blood glucose concentration.

Briefly, according to an embodiment, a comparison of a rate of change in blood glucose concentration as observed from blood glucose sensor measurements with a rate of change in blood glucose concentration as observed from blood glucose reference samples may be expressed as a point in a polar plot or graph. The polar plot or graph may then be generated onto a visual medium to allow for convenient analysis of the performance of a blood glucose sensor under certain conditions. For example, the visual plot may be used for evaluating a blood glucose sensor's ability to accurately observe a rate of change in a patient's blood glucose concentration under certain critical conditions.

In one implementation, a special purpose computing platform may perform computations to generate signals for presentation of a polar plots on a visual medium such as, for example, images on a computer display, images on printed documents, digital images for transmission in a transmission medium or storage in a storage medium in a compressed format. It should be understood, however, that these are merely examples of how a special purpose computing platform may generate signal for presentation of a polar plot on a visual medium, and that claimed subject matter is not limited in this respect.

Figure 1:
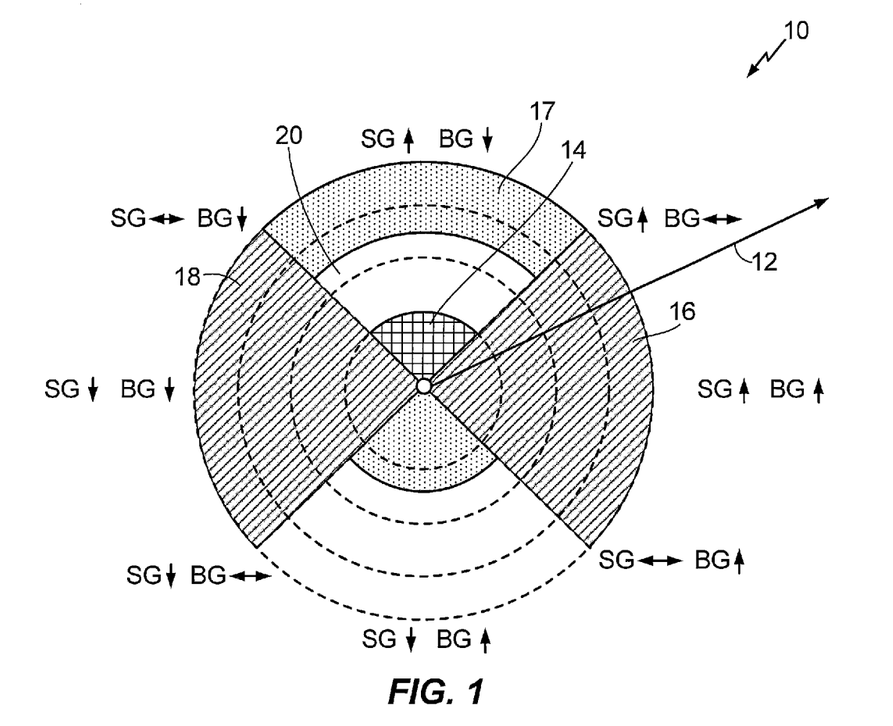
FIG. 1 is a polar plot expressing a comparison between a rate of change in sensor blood glucose and a rate of change in reference blood glucose according to an embodiment.

FIG. 1 is a polar plot expressing a comparison between a rate of change in a blood glucose concentration as observed from a glucose sensor and a rate of change in the blood glucose concentration as reference blood glucose according to an embodiment. Here, a "polar plot" may comprise a graphical representation of multi-dimensional values. In one particular example, a two-dimensional polar plot may express points or values defined by a radius from an origin and an angle about the origin from a reference angle. In the particular implementation of FIG. 1, points are plotted based, at least in part, on a current observation of a patient's blood glucose concentration and a metric comparing a current rate of change of blood glucose concentration as observed by a blood glucose sensor and a current rate of change of blood glucose concentration as observed from blood glucose reference sample. Here, a point on the plot of FIG. 1 expresses an observed blood glucose concentration as a radius from the origin to the point and may express a relative comparison of rate of change of blood glucose concentration (as observed from a blood glucose sensor and as observed from blood glucose reference measurements) as an angle. In a particular implementation, the radius from the origin represents an observed magnitude of blood glucose concentration based on a blood glucose reference sample. The angle to represent the relative comparison of observed rates of change may be computed using any one of several techniques as discussed below.

Blood glucose reference samples may be obtained using any one of several techniques such as from a blood glucose meter that receives blood glucose samples from finger sticks, etc. Other techniques for obtaining blood glucose reference samples may include, for example, blood gas analyzers and glucose chemistry analyzers that utilize venous or arterial blood samples. While possibly providing less frequent measurements of blood glucose concentration than a blood glucose sensor performing continuous glucose monitoring, a blood glucose reference sample used in a discrete blood glucose meter may provide a more accurate and/or reliable measurement of a patient's blood glucose concentration at a sample time than a measurement of the blood glucose concentration from a continuous blood glucose sensor. As such, blood glucose reference samples may be obtained from time to time to calibrate a blood glucose sensor as described in U.S. patent application Ser. No. 13/239,265, filed on Sep. 21, 2011, and assigned to the assignee of claimed subject matter. An angle of points in plot 10 may allow for a convenient assessment of how well a blood glucose sensor is observing a trend in blood glucose level (e.g., rate of increase or decrease) as compared with a process to observe the trend in blood glucose level based on presumably reliable and accurate blood glucose reference measurements.

As a relative comparison of observed rates of change may be expressed as an angle, plot 10 in FIG. 1 may be partitioned into four quadrants as follows: (1) a rate of change in blood glucose concentration as observed from a blood glucose sensor and as observed from blood glucose reference samples are both positive (SG↑BG↑); (2) a rate of change in blood glucose concentration as observed from a blood glucose sensor is positive while a rate of change in blood glucose concentration observed from blood glucose reference samples is negative (SG↑BG↓); (3) a rate of change in blood glucose concentration as observed from a blood glucose sensor and as observed from blood glucose reference samples are both negative (SG↓BG↓); and (4) a rate of change in blood glucose concentration as observed from a blood glucose sensor is negative while a rate of change in blood glucose concentration observed from blood glucose reference samples is positive (SG↓BG↑). Additionally, plot 10 may be partitioned into concentric sections to represent certain glycemic conditions of interest. For example, region 20 may represent a target blood glucose range, region 14 may represent a hypoglycemic condition and region 17 may represent a hyperglycemic condition. It should be understood, however, that these are merely example ranges that may reflect glycemic conditions of interest and claimed subject matter is not limited in this respect.

Plot 10 may also be partitioned according to both angle (representing relative rates of change of blood glucose concentration observed from a blood glucose sensor and observed from blood glucose reference samples) and radial distance from the origin (observed blood glucose concentration level). As discussed below, points in region 14 and in quadrant SG↑BG↓ (a blood glucose sensor observes blood glucose concentration to be rising while the blood glucose concentration is observed to be falling according to blood glucose reference samples) may present a dangerous condition if computation of commands to an insulin infusion pump relies on a trend in blood glucose level observed by a blood glucose sensor, for example.

As pointed out above, a controller computing commands for the infusion of insulin from a pump may rely on a rate of change in blood glucose as observed by a blood glucose sensor. For example, if a blood glucose concentration is observed to be in a target range but observed to be trending higher, a controller may generate a command to an insulin pump to increase a rate of insulin infusion. Likewise, if a blood glucose concentration is observed to be in a target range but observed to be trending lower, a controller may generate a command to an insulin pump to decrease a rate of insulin infusion. A trend blood glucose level observed from a blood glucose sensor at a point in quadrant SG↑BG↓ indicates a rising blood glucose level while the actual trend (e.g., as observed from blood glucose reference samples) may indicate a falling blood glucose level. If the point is also in hypoglycemic region 14, reliance on this rising blood glucose level observed by the blood glucose sensor may lead to an infusion of insulin possibly leading to dangerous conditions such as hypoglycemic shock.

As pointed out above, an angle of a plotted point may be determined based, at least in part, on a metric comparing a current rate of change of blood glucose concentration as observed by a blood glucose sensor and a current rate of change of blood glucose concentration as observed from blood glucose reference samples. In the particular implementation of FIG. 1, an angle of a plotted a point θ may be determined as follows:

$$\theta = \arctan(ROC_{SG}/ROC_{BG}),$$

where:
$ROC_{BG}$ is a current rate of change of blood glucose concentration as observed from a blood glucose sensor; and
$ROC_{BG}$ is a current rate of change of blood glucose concentration as observed from blood glucose reference samples.

In one particular implementation, $ROC_{SG}$ and $ROC_{BG}$ for mapping an angle of a plotted point may be determined from an observed change in blood glucose over a time interval (e.g., one hour). For example, $ROC_{SG}$ or $ROC_{BG}$ may be computed based on a difference in observed blood glucose concentration over the time interval divided by the time interval. A radius of the plotted point from the origin may then be determined as a blood glucose concentration observed from a blood glucose reference sample at the end of the time interval.

In alternative embodiments, $ROC_{SG}$ or $ROC_{BG}$ may be computed using any one of several techniques for computing a rate of change of a signal in the presence of noise. For example, a Savitzky-Golay filter, as discussed in Savitzky, A;

Golay, M J E: Smoothing and differentiation of data by simplified least squares procedures, Analytical Chemistry 1964; 36 (8): 1627-1639, may be used to compute a rate of change by performing a local polynomial regression of degree Mona series of values (e.g., of at least M+1 values equally spaced). In another particular implementation, a Fourier decomposition may be used to compute a first derivative in the frequency domain as discussed in Jauberteau, F; Jauberteau, J L: Numerical differentiation with noisy signal, Applied Mathematics and Computation 2009; 215: 2283-2297. It should be understood, however, that these are merely examples of techniques for computing a rate of change of a signal in the presence of noise, and claimed subject matter is not limited to any particular technique.

Figure 2:
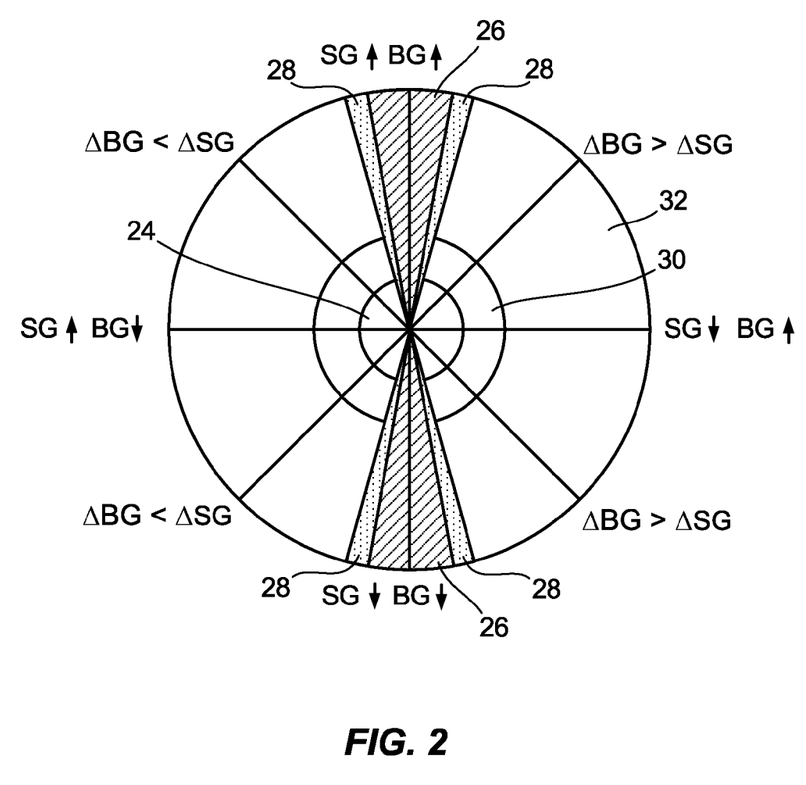
FIGS. 2 and 3 are polar plots expressing a comparison between a rate of change in sensor blood glucose and a rate of change in reference blood glucose according to an alternative embodiment.

FIG. 2 shows an alternative embodiment in which an angle of a plotted point is determined based, at least in part, on a vector dot product. Like the embodiment of FIG. 1, a radius of a plotted point may be determined from a blood glucose concentration as observed from one or more blood glucose reference samples. However, points in the plot of FIG. 2 may be plotted at an angle Ψ to be determined as follows:

$$\Psi = \cos^{-1}\left[\frac{ROC_{BG} \cdot ROC_{SG}}{\|ROC_{BG}\|\|ROC_{SG}\|}\right].$$

Points in region 30 may indicate that a patient's blood glucose is in a target blood glucose range while region 24 may indicate a hypoglycemic condition and region 32 may indicate a hyperglycemic condition. Like the polar plot of FIG. 1, the polar plot of FIG. 2 is partitioned into quadrants SG↑BG↑, SG↑BG↓, SG↓BG↓ and SG↓BG↑. As suggested above with reference to FIG. 1, points in a portion of region 24 that are also in quadrant SG↓BG↑ may be indicative of a sensor indicating a rising blood glucose level while an actual trend (e.g., as observed from blood glucose reference samples) may indicate a falling blood glucose level. Again, reliance on this rising blood glucose level observed by the blood glucose sensor may lead to an infusion of insulin possibly leading to dangerous conditions such as hypoglycemic shock.

Figure 3:
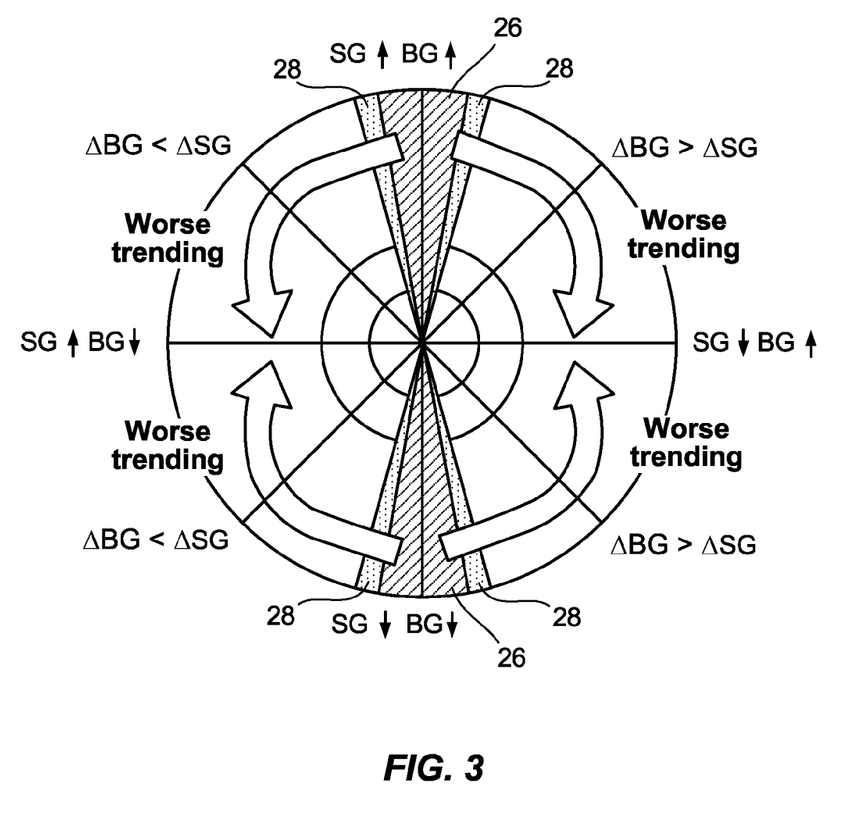

A line bisecting quadrants SG↑BG↑ and SG↓BG↓ in the polar plot of FIG. 2 may define an ideal agreement between rates of change in a patient's blood glucose concentration as observed from continuous blood glucose monitoring and blood glucose reference samples. As illustrated in FIG. 3, as plotted points angularly deviate outward from this line, it may be inferred that performance of a blood glucose sensor in observing a rate of change is degrading. In a particular example, points in an angular region 26 about the line bisecting quadrants SG↑BG↑ and SG↓BG↓ may be indicative of good performance of a blood glucose sensor in observing a change in blood glucose concentration. Points in radial region 28, extending angularly further from the line bisecting quadrants SG↑BG↑ and SG↓BG↓, may be indicative of a degraded yet acceptable performance of a blood glucose sensor in observing a change in blood glucose concentration.

Figure 4:
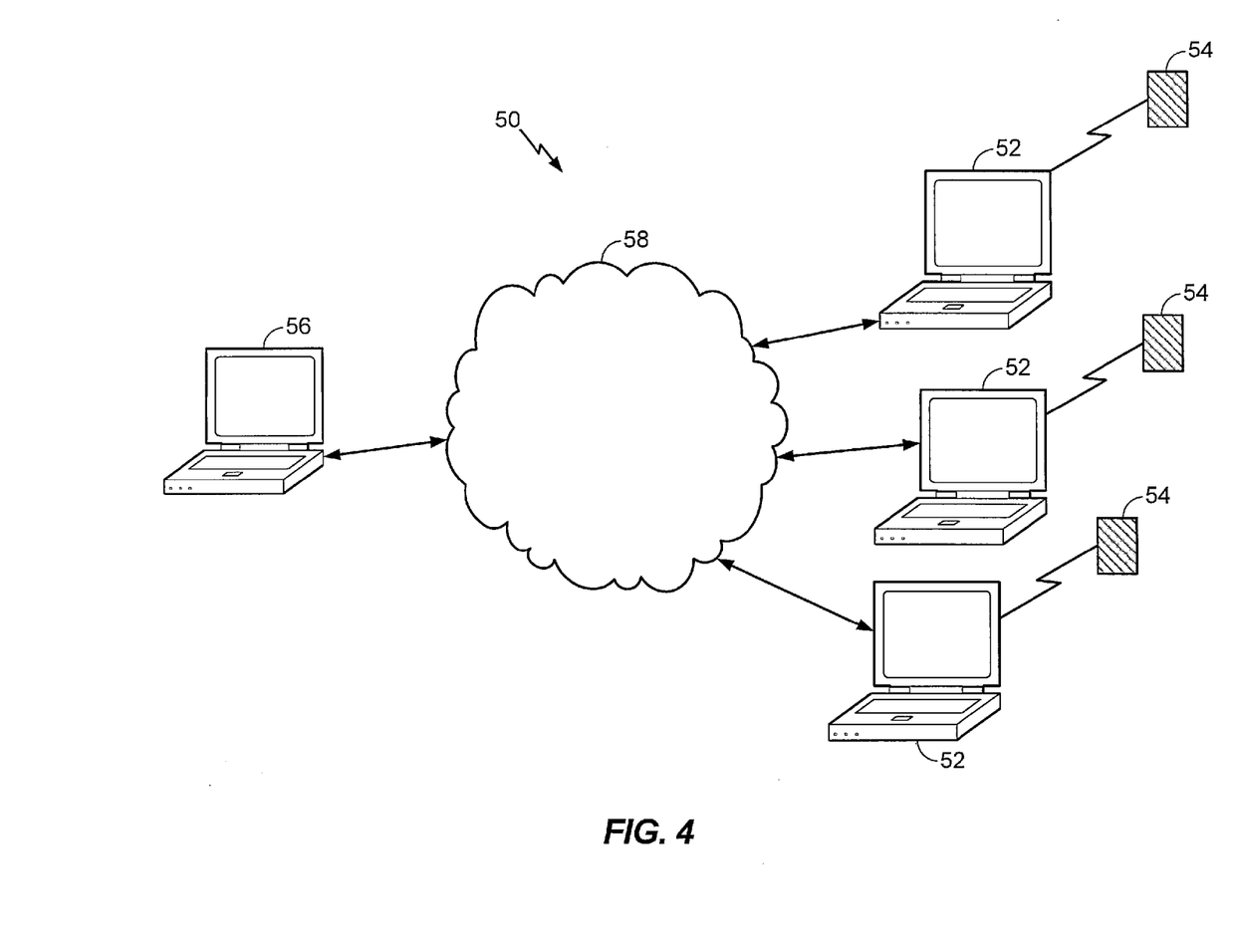
FIG. 4 is a schematic diagram of a system for collecting and processing blood glucose measurements from multiple patients according to an embodiment.

FIG. 4 is a schematic diagram of a system 50 comprising a computing environment according to an embodiment for computing a presenting a polar plot for presentation on a visual medium. Computing platforms 52 may be communicatively coupled to computing platform 56 through network 58. Computing platforms 52 and 56 may have communication interface components to facilitate communication with other devices through network 58 including, for example, modems, network adapters, and/or the like. Network 58 may comprise any one of several combinations of wired and wireless communication infrastructure including, for example, wired and wireless wide area network infrastructure and/or local area network infrastructure. In a particular implementation, network 58 may provide Internet protocol infrastructure to facilitate communication between computing platform 56 and computing platforms 52 in TCP/IP sessions, HTML, XML or other web service paradigms, for example.

Computing platforms 52 and 56 may comprise processors, memory, input/output devices, display devices, etc., to enable or support applications. For example, a memory may store instructions that are executable by a processor to perform one or more functions, tasks, processes, etc. In particular implementations, computing platforms 52 and 56 may comprise any one of several types of computing devices such as, for example, a server, personal computing, notebook computer, cell phone, smart phone, just to provide a few examples. Computing platforms 52 and 56 may comprise a graphical user interface (GUI) that facilitates user interaction with applications.

In a particular implementation, computing platforms 52 may be communicatively coupled (e.g., wired or wirelessly) to blood glucose monitoring device 54 to receive measurements of a patient's blood glucose concentration. Blood glucose monitoring device 54 may comprise a blood glucose meter capable of receiving blood glucose samples (e.g., from test strips). In another embodiment, blood glucose monitoring device 54 may comprise a blood glucose sensor and monitor for providing continuous blood glucose concentration measurements from processing signals from a blood glucose sensor as described below in a particular implementation with reference to FIGS. 5 through 8. Such a continuous blood glucose monitor may also be capable of receiving blood glucose reference measurements through a user interface, for example. A combination of blood glucose reference measurements and measurements obtained from a blood glucose sensor may be received at monitoring device 54. These measurements may be stored in a storage medium for computing a polar plot for presentation on a visual medium as discussed above.

Computing platforms 52 may be coupled to corresponding blood glucose monitoring devices 54 using a wired or wireless link such as, for example, a universal serial bus, Bluetooth link, ultra wideband link, IEEE Std. 802.11 link, just to provide a few examples. In one example, a monitoring device 54 may comprise a memory (not shown) to store a history of blood glucose concentration measurements to be downloaded to a computing platform 52. Alternatively, a blood glucose monitoring device 54 may forward blood glucose concentration measurements to a computing platform 52 as such blood glucose measurements are received in real-time.

In one implementation, system 50 may be located in a hospital environment where computing platforms 52 are co-located with patients at different locations communicate with a central computing platform 56 to centrally collect and process patient data. In another implementation, system 50 may be more geographically distributed in that central computing platform 50 may be located in doctor's office or medical clinic while computing platforms 52 are located in patients' homes. Here, a polar plot may be computed and presented for each patient to assess the performance of its glucose monitor.

Figure 5:
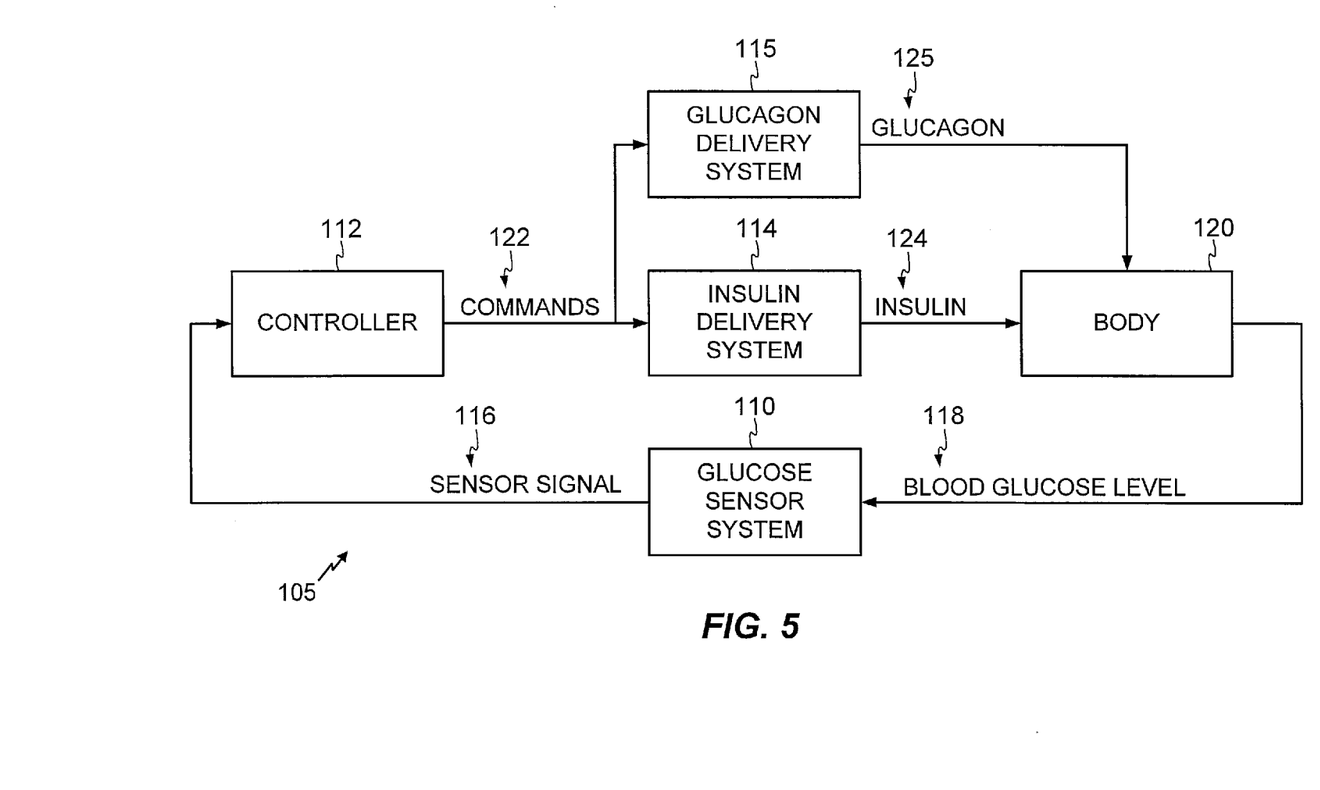
FIG. 5 is a schematic diagram of an example closed loop glucose control system in accordance with an embodiment.

FIG. 5 is a block diagram of an example closed loop glucose control system 105 in accordance with an embodiment. Particular embodiments may include a glucose sensor system 110, a controller 112, an insulin delivery system 114, and a glucagon delivery system 115, etc. as shown in FIG. 5. In certain example embodiments, glucose sensor system 110 may generate a sensor signal 116 representative of blood glucose levels 118 in body 120, and glucose sensor system 110 may provide sensor signal 116 to controller 112. Controller 112 may receive sensor signal 116 and generate commands 122 that are communicated at least to insulin delivery system 114 and/or glucagon delivery system 115. Insulin delivery system 114 may receive commands 122 and infuse insulin 124 into body 120 in response to commands 122. Likewise, glucagon delivery system 115 may receive commands 122 from controller 112 and infuse glucagon 125 into body 120 in response to commands 122.

Glucose sensor system 110 may include, by way of example but not limitation, a glucose sensor; sensor electrical components to provide power to a glucose sensor and to generate sensor signal 116; a sensor communication system to carry sensor signal 116 to controller 112; a sensor system housing for holding, covering, and/or containing electrical components and a sensor communication system; any combination thereof, and so forth.

Controller 112 may include, by way of example but not limitation, electrical components, other hardware, firmware, and/or software, etc. to generate commands 122 for insulin delivery system 114 and/or glucagon delivery system 115 based at least partly on sensor signal 116. Controller 112 may also include a controller communication system to receive sensor signal 116 and/or to provide commands 122 to insulin delivery system 114 and/or glucagon delivery system 115. In particular example implementations, controller 112 may include a user interface and/or operator interface (not shown) comprising a data input device and/or a data output device. Such a data output device may, for example, generate signals to initiate an alarm and/or include a display or printer for showing a status of controller 112 and/or a patient's vital indicators, monitored historical data, combinations thereof, and so forth. Such a data input device may comprise dials, buttons, pointing devices, manual switches, alphanumeric keys, a touch-sensitive display, combinations thereof, and/or the like for receiving user and/or operator inputs. It should be understood, however, that these are merely examples of input and output devices that may be a part of an operator and/or user interface and that claimed subject matter is not limited in these respects. In another embodiment, controller 112 may comprise an input device for receiving blood glucose reference sample measurements for use in, for example, computing a polar plot as described above.

Insulin delivery system 114 may include an infusion device and/or an infusion tube to infuse insulin 124 into body 120. Similarly, glucagon delivery system 115 may include an infusion device and/or an infusion tube to infuse glucagon 125 into body 120. In alternative embodiments, insulin 124 and glucagon 125 may be infused into body 120 using a shared infusion tube. In other alternative embodiments, insulin 124 and/or glucagon 125 may be infused using an intravenous system for providing fluids to a patient (e.g., in a hospital or other medical environment). While an intravenous system is employed, glucose may be infused directly into a bloodstream of a body instead of or in addition to infusing glucagon into interstitial tissue. It should also be understood that certain example embodiments for closed loop glucose control system 105 may include an insulin delivery system 114 without a glucagon delivery system 115 (or vice versa).

In particular example embodiments, an infusion device (not explicitly identified in FIG. 5) may include electrical components to activate an infusion motor according to commands 122; an infusion communication system to receive commands 122 from controller 112; an infusion device housing (not shown) to hold, cover, and/or contain the infusion device; any combination thereof; and so forth.

In particular example embodiments, controller 112 may be housed in an infusion device housing, and an infusion communication system may comprise an electrical trace or a wire that carries commands 122 from controller 112 to an infusion device. In alternative embodiments, controller 112 may be housed in a sensor system housing, and a sensor communication system may comprise an electrical trace or a wire that carries sensor signal 116 from sensor electrical components to controller electrical components. In other alternative embodiments, controller 112 may have its own housing or may be included in a supplemental device. In yet other alternative embodiments, controller 112 may be co-located with an infusion device and a sensor system within one shared housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Figure 6:
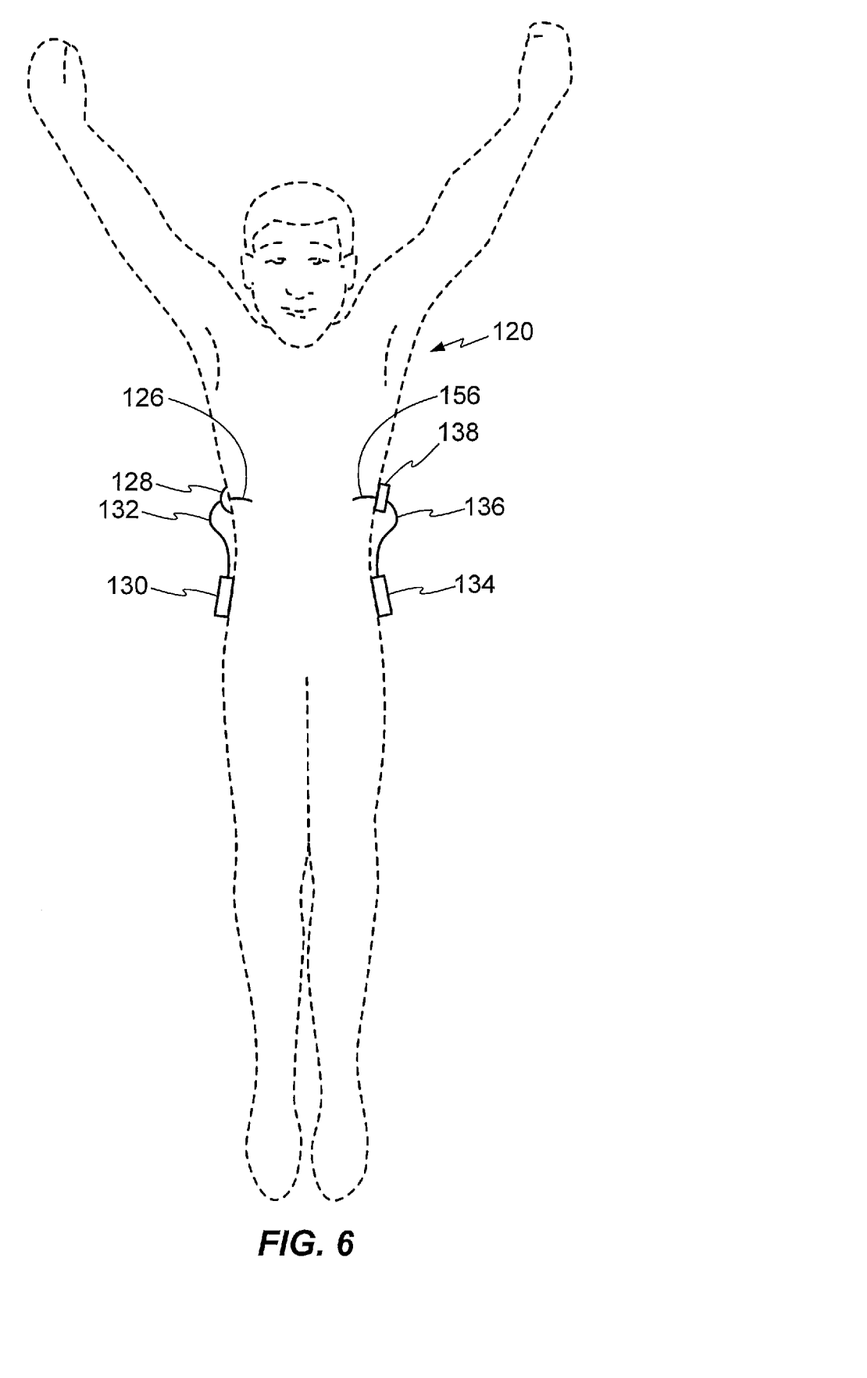
FIG. 6 is a front view of example closed loop hardware located on a body in accordance with an embodiment.
Figures 7A, 7B:
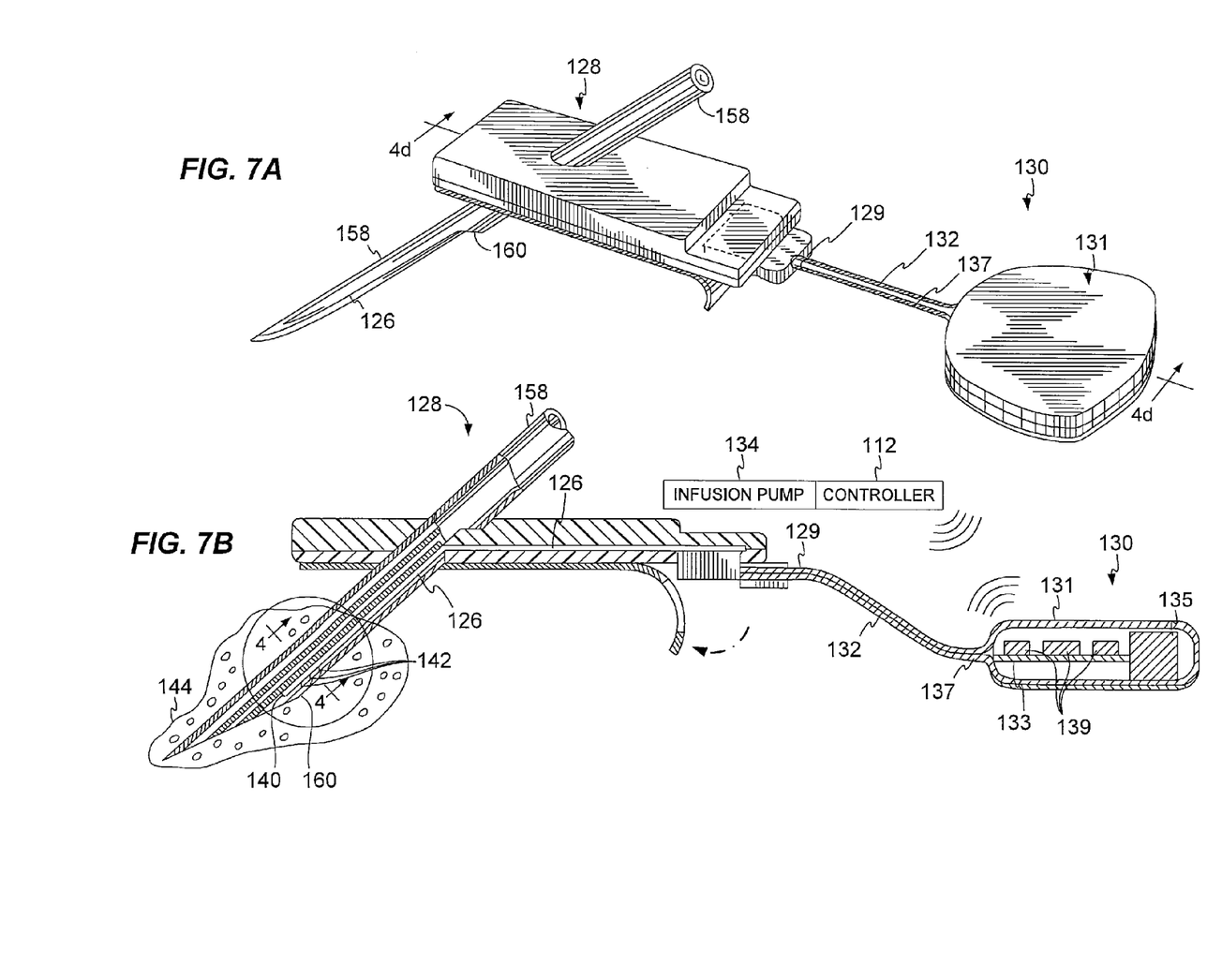
FIG. 7(a) is a perspective view of an example glucose sensor system for use in accordance with an embodiment.
FIG. 7(b) is a side cross-sectional view of a glucose sensor system of FIG. 10(a) for an embodiment.
Figure 7C:
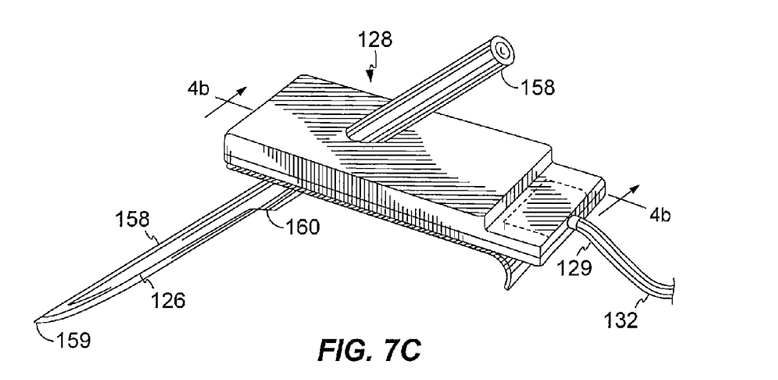
FIG. 7(c) is a perspective view of an example sensor set for a glucose sensor system of FIG. 7(a) for use in accordance with an embodiment.
Figure 7D:
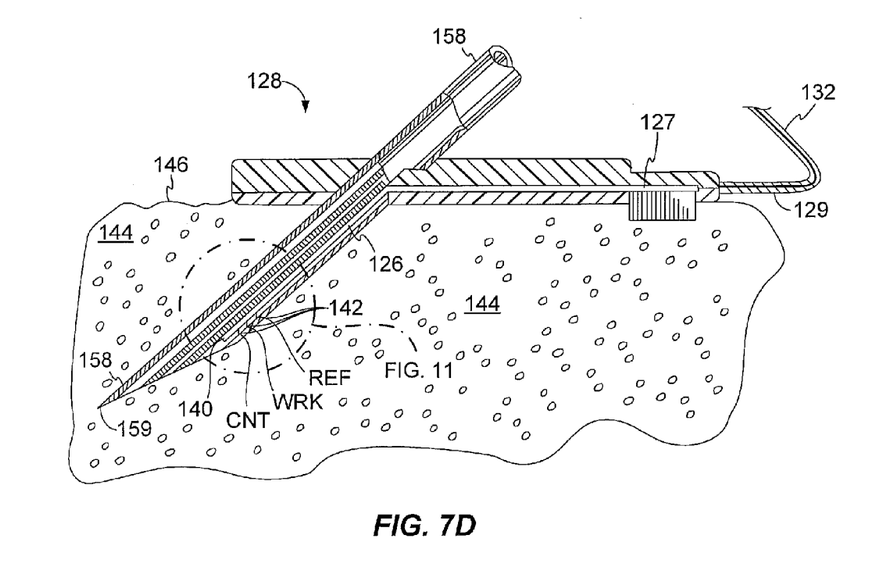
FIG. 7(d) is a side cross-sectional view of a sensor set of FIG. 7(c) for an embodiment.
Figure 8:
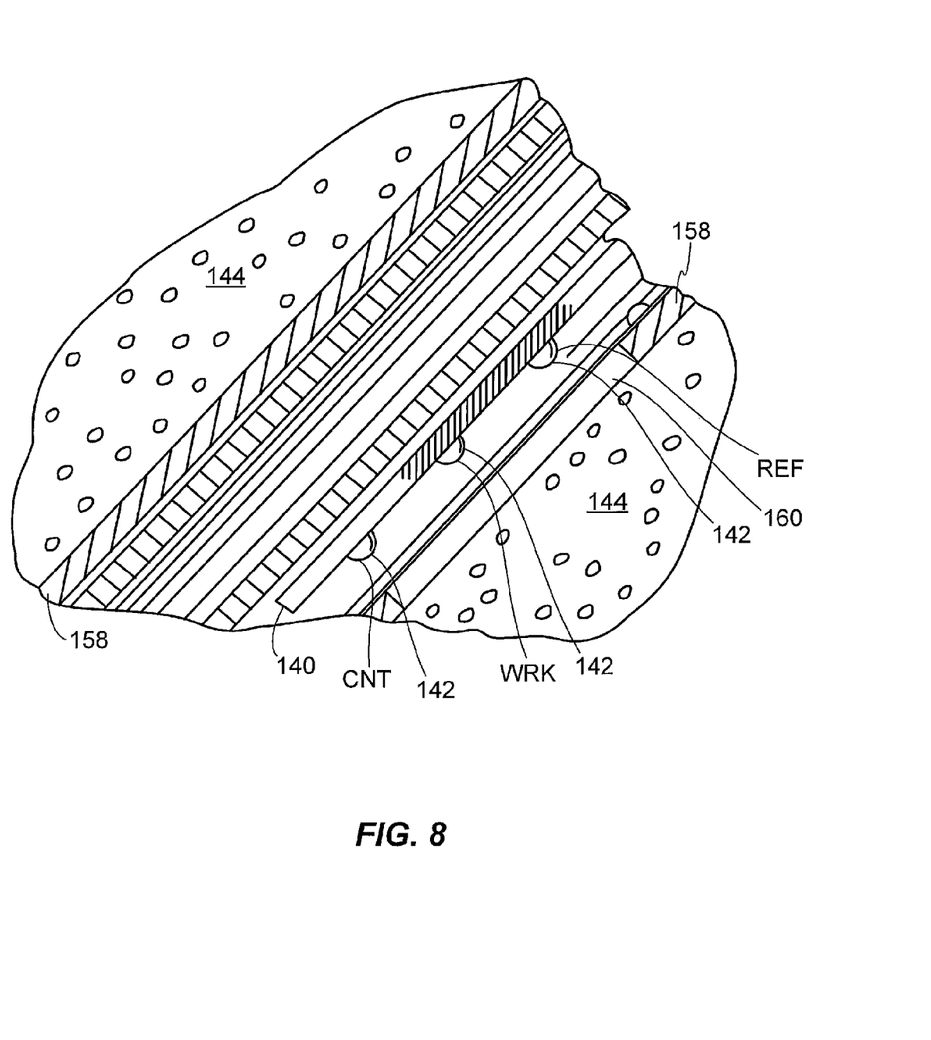
FIG. 8 is a cross sectional view of an example sensing end of a sensor set of FIG. 7(d) for use in accordance with an embodiment.
Figure 9:
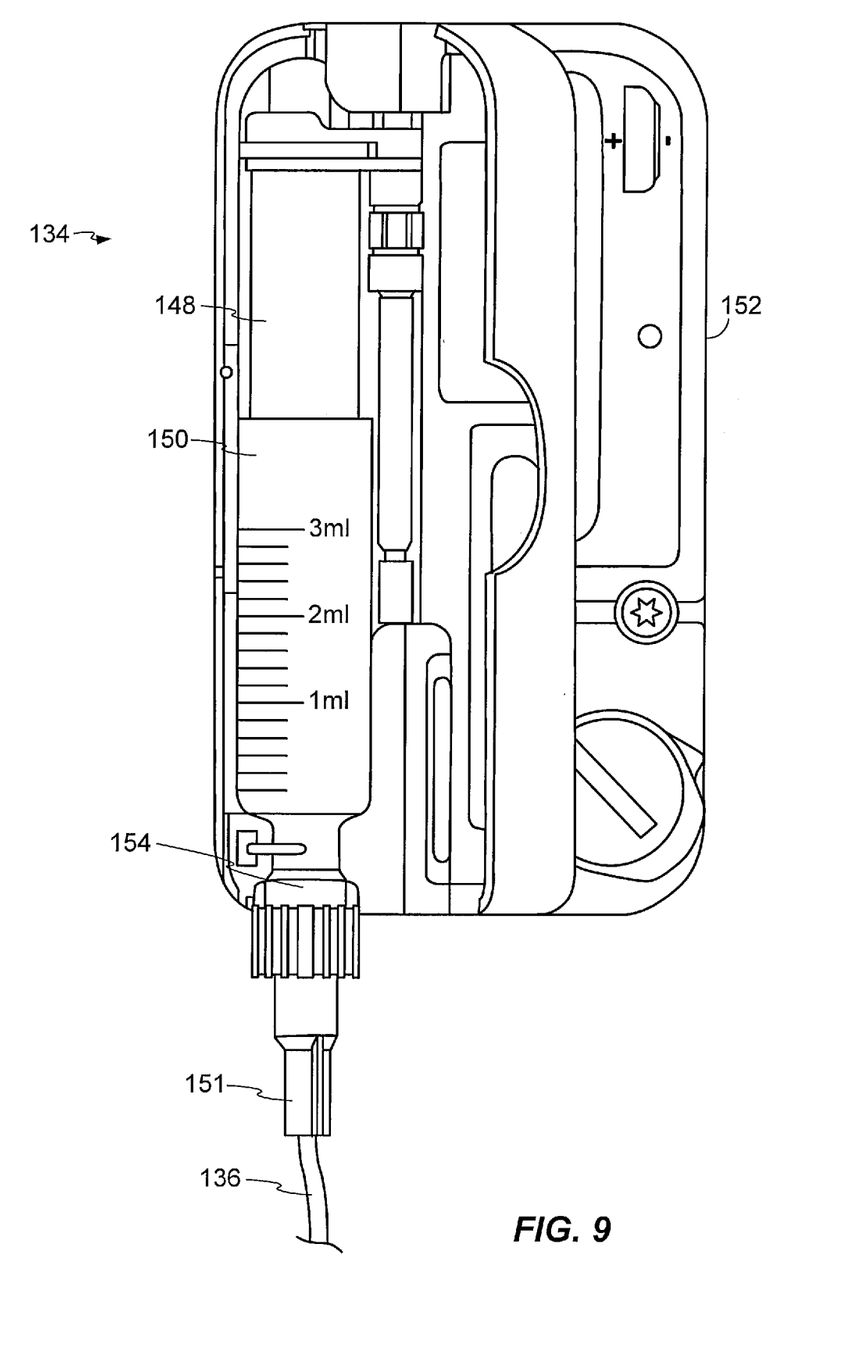
FIG. 9 is a top view of an example infusion device with a reservoir door in an open position, for use according to an embodiment.
Figure 10:
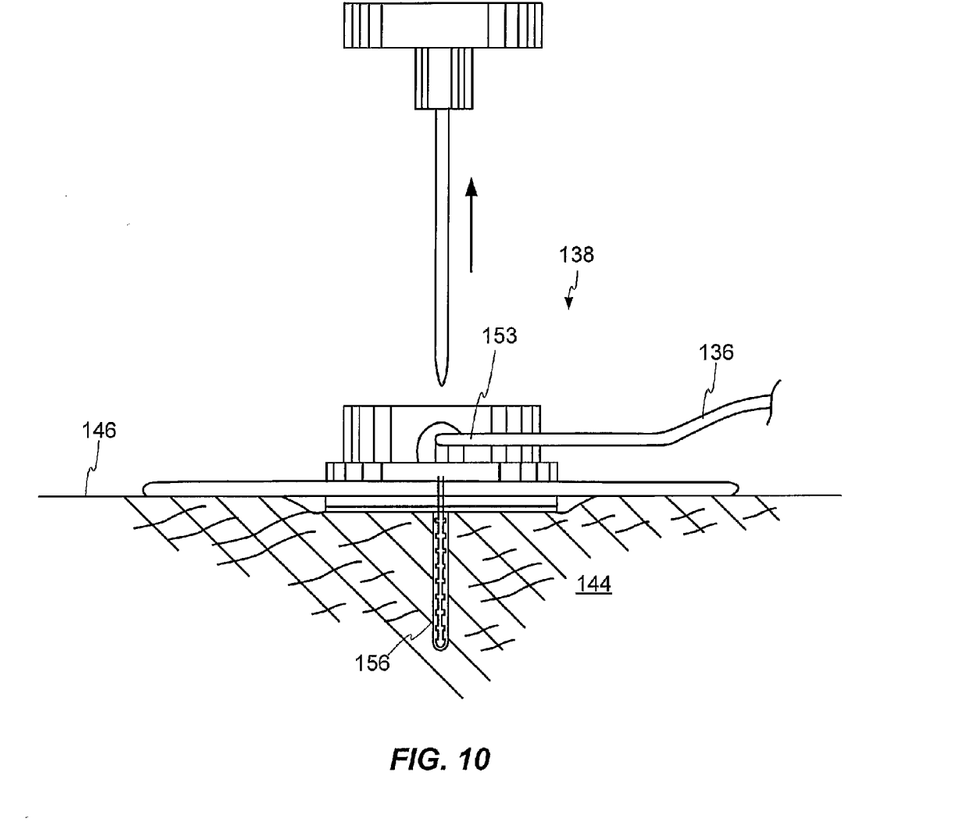
FIG. 10 is a side view of an example infusion set with an insertion needle pulled out, for use according to an embodiment.

FIGS. 6 through 10 illustrate example glucose control systems in accordance with certain embodiments. FIG. 6 is a front view of example closed loop hardware located on a body in accordance with certain embodiments. FIGS. 7(a)-7(d) and 8 show different views and portions of an example glucose sensor system for use in accordance with certain embodiments. FIG. 9 is a top view of an example infusion device with a reservoir door in an open position in accordance with certain embodiments. FIG. 10 is a side view of an example infusion set with an insertion needle pulled out in accordance with certain embodiments.

Particular example embodiments may include a sensor 126, a sensor set 128, a telemetered characteristic monitor 130, a sensor cable 132, an infusion device 134, an infusion tube 136, and an infusion set 138, any or all of which may be worn on a body 120 of a user or patient, as shown in FIG. 6. As shown in FIGS. 7(a) and 7(b), telemetered characteristic monitor 130 may include a monitor housing 131 that supports a printed circuit board 133, battery or batteries 135, antenna (not shown), a sensor cable connector (not shown), and so forth. A sensing end 140 of sensor 126 may have exposed electrodes 142 that may be inserted through skin 146 into a subcutaneous tissue 144 of a user's body 120, as shown in FIGS. 7(d) and 8. Electrodes 142 may be in contact with interstitial fluid (ISF) that is usually present throughout subcutaneous tissue 144.

Sensor 126 may be held in place by sensor set 128, which may be adhesively secured to a user's skin 146, as shown in FIGS. 7(c) and 7(d). Sensor set 128 may provide for a connector end 127 of sensor 126 to connect to a first end 129 of sensor cable 132. A second end 137 of sensor cable 132 may connect to monitor housing 131. Batteries 135 that may be included in monitor housing 131 provide power for sensor 126 and electrical components 139 on printed circuit board 133. Electrical components 139 may sample a current of sensor signal 116 (e.g., of FIG. 5) to provide digital sensor values (Dsig) and store Dsig values in a memory. Digital sensor values Dsig may be periodically transmitted from a memory to controller 112, which may be included in an infusion device.

In a particular implementation, controller 112 may perform additional filtering and processing on values for Dsig to compute continuous sensor blood glucose measurements as described in U.S. patent application Ser. No. 12/345,477, filed on Dec. 29, 2008, and Ser. No. 12/347,716, filed on Dec. 31, 2008, assigned to the assignee of claimed subject matter and incorporated herein by reference.

With reference to FIGS. 5, 6 and 9, a controller 112 may process digital sensor values Dsig and generate commands 122 for infusion device 134. Infusion device 134 may respond to commands 122 and actuate a plunger 148 that forces insulin 124 out of a reservoir 150 that is located inside an infusion device 134. Glucose may be delivered from a reservoir responsive to commands 122 using a similar and/or analogous device (not shown). In alternative implementations, glucose may be administered to a patient orally.

In particular example embodiments, a connector tip 154 of reservoir 150 may extend through infusion device housing 152, and a first end 151 of infusion tube 136 may be attached to connector tip 154. A second end 153 of infusion tube 136 may connect to infusion set 138 (e.g., of FIGS. 6 and 10). Insulin 124 may be forced through infusion tube 136 into infusion set 138 and into body 116. Infusion set 138 may be adhesively attached to a user's skin 146. As part of infusion set 138, a cannula 156 may extend through skin 146 and terminate in subcutaneous tissue 144 to complete fluid communication between a reservoir 150 and subcutaneous tissue 144 of a user's body 116.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggybacks off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, anticoagulants, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 126, sensor set 128, telemetered characteristic monitor 130, sensor cable 132, infusion tube 136, infusion set 138, and so forth. Instead, standard blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed 15 May 2008, may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Controller 112, and computing devices 52 and 56 may comprise one or more processors capable of executing instructions to thereby render controller 112, or computing devices 52 and 56 a special purpose computing device to perform algorithms, functions, methods, etc.; to implement attributes, features, etc.; and so forth that are described herein.

Such processor(s) may be realized as microprocessors, digital signal processors (DSPs), application specific integrated circuits (ASICs), programmable logic devices (PLDs), controllers, micro-controllers, a combination thereof, and so forth, just to name a few examples. Alternatively, an article may comprise at least one storage medium (e.g., such as one or more memories) having stored thereon instructions 1706 that are executable by one or more processors.

Unless specifically stated otherwise, as is apparent from the preceding discussion, it is to be appreciated that throughout this specification discussions utilizing terms such as "processing", "computing", "calculating", "determining", "assessing", "estimating", "identifying", "obtaining", "representing", "receiving", "transmitting", "storing", "analyzing", "measuring", "detecting", "controlling", "delaying", "initiating", "providing", "performing", "generating", "altering" and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be understood that aspects described above are examples only and that embodiments may differ there from without departing from claimed subject matter. Also, it should be noted that although aspects of the above systems, methods, apparatuses, devices, processes, etc. have been described in particular orders and in particular arrangements, such specific orders and arrangements are merely examples and claimed subject matter is not limited to the orders and arrangements as described. It should additionally be noted that systems, devices, methods, apparatuses, processes, etc. described herein may be capable of being performed by one or more computing platforms.

In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although there have been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method comprising:
   obtaining a plurality of blood glucose reference samples from a patient;
   obtaining a plurality of glucose sensor measurements using a glucose sensor in contact with the patient;
   computing a first rate of change in blood glucose concentration as observed from two or more of the plurality of blood glucose reference samples;
   computing a second rate of change in the blood glucose concentration as observed from two or more of the plurality of glucose sensor measurements;
   generating an angular coordinate and a radial coordinate of a polar plot,
      wherein the angular coordinate is a function of the first rate of change and the second rate of change, and
      wherein the radial coordinate is proportional to a magnitude of a blood glucose concentration of the patient as measured from one or more of the plurality of blood glucose reference samples; and
   generating signals to present a graphical representation of a value on the polar plot in a visual medium, wherein the value corresponds to the angular coordinate and the radial coordinate, and
   wherein the computing the first rate of change, the computing the second rate of change, the generating the angular coordinate and the radial coordinate, and the generating signals to present the graphical representation are performed by one or more processors.

2. The method of claim 1, and further comprising defining an alert region of the polar plot comprising a hypoglycemic region within a threshold radius and an angular section defined, at least in part, by a positive rate of change in blood glucose according to the second rate of change and a negative rate of change according to the first rate of change.

3. The method of claim 1, wherein the angular coordinate is based, at least in part, on the arctangent of a ratio of the second rate of change to the first rate of change.

4. The method of claim 1, wherein the visual medium comprises a printed document.

5. The method of claim 1, wherein the visual medium comprises an image presented on a computer display.

6. The method of claim 1, wherein the computing the second rate of change further comprises:
   obtaining a first value associated with a first blood glucose reference sample of the plurality of blood glucose reference samples at a beginning of a period;
   obtaining a second value associated with a second blood glucose reference sample of the plurality of blood glucose reference samples at an end of the period; and
   dividing a difference between the first and second values by the period.

7. The method of claim 6, wherein the radial coordinate is proportional to a magnitude of a blood glucose concentration of the second blood glucose reference sample.

8. A computing platform for use with a glucose sensor in contact with a patient, comprising:
   one or more processors to:
      receive a first plurality of signals generated in response to a plurality of blood glucose reference samples from the patient;
      receive a second plurality of signals generated in response to a plurality of glucose sensor measurements using the glucose sensor in contact with the patient;
      compute a first rate of change in blood glucose concentration based, at least in part, on two or more of the plurality of blood glucose reference samples;
      compute a second rate of change in the blood glucose concentration based, at least in part, on two or more of the plurality of glucose sensor measurements;
      generate an angular coordinate and a radial coordinate of a polar plot,
         wherein the angular coordinate is a function of the first rate of change and the second rate of change, and
         wherein the radial coordinate is proportional to a magnitude of a blood glucose concentration of the patient as measured from one or more of the plurality of blood glucose reference samples; and
      generate signals to present a graphical representation of a value on the polar plot in a visual medium, wherein the value corresponds to the angular coordinate and the radial coordinate.

9. The computing platform of claim 8, and further comprising a display device to present an image of the graphical representation responsive to the generated signals.

10. The computing platform of claim 8, and further comprising a storage medium to store a digital image of the graphical representation in a compressed format.

11. The computing platform of claim 8, wherein the signals comprise commands to a printer for printing the graphical representation onto a printed document.

12. The computing platform of claim 8, and further comprising a communication device, the one or more processors further to initiate transmission of the generated signals to a communication network.

13. An article for use with a glucose sensor in contact with a patient, comprising:
   a non-transitory storage medium comprising machine-readable instructions stored thereon which are executable by a special purpose computing apparatus to:
      receive a first plurality of signals generated in response to a plurality of blood glucose reference samples from the patient;
      receive a second plurality of signals generated in response to a plurality of glucose sensor measurements using the glucose sensor in contact with the patient;
      compute a first rate of change in blood glucose concentration based, at least in part, on two or more of the plurality of blood glucose reference samples;
      compute a second rate of change in the blood glucose concentration based, at least in part, on two or more of the plurality of glucose sensor measurements;
      generate an angular coordinate and a radial coordinate of a polar plot, wherein the angular coordinate is a function of the first rate of change and the second rate of change; and wherein the radial coordinate is proportional to a magnitude of a blood glucose concentration of the patient as measured from one or more of the plurality of blood glucose reference samples; and generate signals to present a graphical representation of a value on the polar plot in a visual medium, wherein the value corresponds to the angular coordinate and the radial coordinate.

14. The article of claim 13, wherein the instructions are further executable by the special purpose computing apparatus to compress a digital image of the graphical representation in a format for storage in a non-transitory storage medium or for transmission in a communication network.

15. The article of claim 13, wherein the instructions are further executable by the special purpose computing apparatus to compute the second rate of change by:
obtaining a first value associated with a first blood glucose reference sample of the plurality of blood glucose reference samples at a beginning of a period;
obtaining a second value associated with a second blood glucose reference sample of the plurality of blood glucose reference samples at an end of the period; and
dividing a difference between the first and second values by the period.

16. The article of claim 15, wherein the radial coordinate is proportional to a magnitude of a blood glucose concentration of the second blood glucose reference sample.

17. The article claim 13, wherein the generated signals comprise signals for presenting an image of the graphical representation on a display.

18. An apparatus for use with a glucose sensor in contact with a patient, comprising:
means for receiving a first plurality of signals generated in response to a plurality of blood glucose reference samples from the patient;
means for receiving a second plurality of signals generated in response to a plurality of glucose sensor measurements using the glucose sensor in contact with the patient;
means for computing a first rate of change in blood glucose concentration based, at least in part, on two or more of the plurality of blood glucose reference samples;
means for computing a second rate of change in the blood glucose concentration based, at least in part, on two or more of the plurality of glucose sensor measurements;
means for generating an angular coordinate and a radial coordinate of a polar plot,
wherein the angular coordinate is a function of the first rate of change and the second rate of change, and
wherein the radial coordinate is proportional to a magnitude of a blood glucose concentration of the patient as measured from one or more of the plurality of blood glucose reference samples; and
means for generating signals to present a graphical representation of a value on the polar plot in a visual medium, wherein the value corresponds to the angular coordinate and the radial coordinate.

* * * * *